United States Patent
Weinstein

(10) Patent No.: US 10,709,686 B2
(45) Date of Patent: Jul. 14, 2020

(54) METHODS FOR TREATING PULMONARY FIBROSIS

(71) Applicant: David Weinstein Consulting, Inc., Dobbs Ferry, NY (US)

(72) Inventor: David Weinstein, Los Altos, CA (US)

(73) Assignee: DAVID WEINSTEIN CONSULTING, INC., Dobbs Ferry, NY (US)

( * ) Notice: Subject to any disclaimer, the term of this patent is extended or adjusted under 35 U.S.C. 154(b) by 0 days.

(21) Appl. No.: 16/358,693

(22) Filed: Mar. 20, 2019

(65) Prior Publication Data

US 2019/0290612 A1 Sep. 26, 2019

Related U.S. Application Data

(60) Provisional application No. 62/645,305, filed on Mar. 20, 2018.

(51) Int. Cl.
| | | |
|---|---|---|
| *A61K 31/40* | (2006.01) | |
| *A61K 9/00* | (2006.01) | |
| *A61P 11/00* | (2006.01) | |
| *A61K 38/13* | (2006.01) | |
| *A61K 31/401* | (2006.01) | |

(52) U.S. Cl.
CPC ............ *A61K 31/40* (2013.01); *A61K 9/0019* (2013.01); *A61K 9/0073* (2013.01); *A61K 31/401* (2013.01); *A61K 38/13* (2013.01); *A61P 11/00* (2018.01)

(58) Field of Classification Search
CPC ...................................................... A61K 31/40
See application file for complete search history.

(56) References Cited

U.S. PATENT DOCUMENTS

| | | | | |
|---|---|---|---|---|
| 6,331,537 B1 * | 12/2001 | Hamilton | ............. | A61K 31/401 514/215 |
| 2013/0090455 A1 * | 4/2013 | Nishio | ................. | C12N 9/0071 530/356 |

OTHER PUBLICATIONS

Nagano et al., European Respiratory Journal, 2006, 27(3): 460-469.*

* cited by examiner

*Primary Examiner* — Rei Tsang Shiao
(74) *Attorney, Agent, or Firm* — Wood, Philips, Katz, Clark & Mortimer

(57) ABSTRACT

The present invention is related to a method of treating idiopathic pulmonary fibrosis comprising administering to a subject in need thereof an effective amount of a composition containing a compound that binds FK506 binding protein 4.

4 Claims, 1 Drawing Sheet
(1 of 1 Drawing Sheet(s) Filed in Color)

METHODS FOR TREATING PULMONARY FIBROSIS

FIELD OF THE INVENTION

The present invention is related to a method of treating idiopathic pulmonary fibrosis comprising administering to a subject in need thereof an effective amount of a composition containing a compound that binds FK506 binding protein 4.

BACKGROUND OF THE INVENTION

Injured mammalian tissues typically heal by a combination of regeneration and repair. Regeneration results in the re-establishment of the original tissue structure and function. In contrast, tissue repair entails the replacement of the original tissue with a patch of connective tissue, or scar, which is functionally and aesthetically inferior to the original (Ferguson M W et al., Scar-free healing: from embryonic mechanisms to adult therapeutic intervention, *Philos Trans R Soc Lond B Biol Sci,* 2004 May 29, 359(1445), 839-850.) The response of most mammalian tissues to injury falls within this spectrum, with some tissues that are believed not to regenerate at all. Regardless of the final outcome—scar or regenerated tissue, wound healing occurs in several stages.

Idiopathic Pulmonary Fibrosis ("IPF") is a hypertrophic scarring response that is initiated following an insult to the alveolar epithelium in the lungs. The local response to the insult initiates the recruitment and proliferation of fibroblasts and myofibroblasts that then form micronodules of scar tissue throughout the affected lung, not unlike the keloid formation in skin. Kuhn, C., 3rd, et al., An immunohistochemical study of architectural remodeling and connective tissue synthesis in pulmonary fibrosis, *Amer Rev. of Resp. Dis.,* 1989, 140, 1693-1703. Once the process is initiated, IPF follows an inevitably fatal course. The mean survival following diagnosis is 2.8 years and the five-year survival is under 12%. The incidence of IPF is estimated at 42 cases per 100,000 population, virtually the same as ovarian or pancreatic cancers. Raghu, G., et al., Incidence and prevalence of idiopathic pulmonary fibrosis, *American journal of respiratory and critical care medicine,* 2006, 174, 810-816; American Cancer Society, *Cancer facts & figures* 2006. At present the therapeutic options are quite limited: there are no agents that effectively alter the course of the disease.

Cyclosporine A ("CSA") was originally developed as an immunosuppressant to prevent solid organ graft rejection in organ transplant recipients. The immunomodulatory activity of cyclosporine is exerted through its tight binding to the calmodulin-dependent, serine/threonine protein phosphatase, calcineurin (Liu J et al., Calcineurin is a common target of cyclophilin-cyclosporine A and FKBP-FK506 complexes, *Cell,* 1991 Aug. 23, 66(4), 807-815.) In T cells, calcineurin/cyclosporine complexes bind to and prevent the nuclear translocation of the nuclear factor of activated T cell ("NFAT") protein, and thus its binding to the interleukin 2 ("IL-2") promoter. This results in a failure to activate IL-2 production, putting an early block on the cellular immune cascade (Harding, 1989; Liu et al., 1991; Schreiber S. et al., Cytokine pattern of Langerhans cells isolated from murine epidermal cell cultures, *J Immunol.* 1992 Dec. 1, 149(11), 3524-3534; Siekierka J J et al., FK-506 and cyclosporin A: immunosuppressive mechanism of action and beyond, *Curr Opin Immunol,* 1992 Oct. 4(5), 548-552. In addition to T cells, NFAT is also highly expressed in stem cells in a number of tissues from embryogenesis through adulthood (Friday B B et al., Calcineurin activity is required for the initiation of skeletal muscle differentiation, *J Cell Biol,* 2000 May 1, 149(3), 657-666; Horsley V et al., Regulation of the growth of multinucleated muscle cells by an NFATC2-dependent pathway, *J Cell Biol,* 2001 Apr. 16, 153(2), 329-38; Horsley V et al., NFAT: ubiquitous regulator of cell differentiation and adaptation, *J Cell Biol,* 2002 Mar. 4, 156(5), 771-774; Li X et al., Calcineurin-NFAT signaling critically regulates early lineage specification in mouse embryonic stem cells and embryos, *Cell Stem Cell,* 2011 Jan. 7, 8(1), 46-58; Zhu L et al., Foxd3 suppresses NFAT-mediated differentiation to maintain self-renewal of embryonic stem cells, EMBO Rep, 2014 December, 15(12), 1286-1296), where it suppresses stem cell differentiation (Horsley V et al., 2002.) This immune suppression and stem cell differentiation modification may be useful in wound healing.

A compound that has been shown to promote wound healing is RT175 (AMG-474-00, GM1485, GPI 1485). RT175 (AMG-474-00, GM1485, GPI 1485) is a 241 Dalton molecule having the following chemical structure

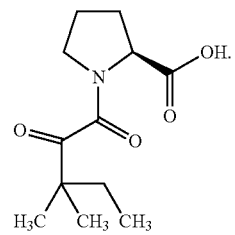

RT175 binds with high affinity to FK506 binding protein 4 ("FKBP52"). FKBP52 is known to act as a molecular chaperone for the glucocorticoid receptor ("GR"). After binding to a ligand, the RT175/GR complex translocates to the nucleus (Banerjee A., et al. Control of glucocorticoid and progesterone receptor subcellular localization by the ligand-binding domain is mediated by distinct interactions with tetratricopeptide repeat proteins, *Biochemistry,* 2008, 47, 10471-10480.) It has been shown that that RT175 treatment of fibroblasts for 2 hours results in the translocation of FKBP52 to the nucleus, presumably with its cargo.

Current wound healing compositions include several inflammation factor compositions such as activated protein C (U.S. Patent Application Publication No. 2014/0219991), hsp90a (U.S. Pat. No. 8,455,443), and FAK inhibitors (U.S. Patent Application Publication No. 2013/0165463) and extracellular matrix replacement such as hyaluronic acid (U.S. Patent Application Publication No. 2015/0064129), sodium hyaluronate (U.S. Pat. No. 8,426,384), zinc gluconate, sodium hyaluronate and collagen (U.S. Pat. No. 9,125,892.)

Due to a lack of effective treatments, there is a need in the art for methods and compositions useful for treating pulmonary fibrosis.

SUMMARY OF THE INVENTION

The present invention is directed to a method of treating idiopathic pulmonary fibrosis comprising administering to a subject in need thereof an effective amount of a composition containing a compound that binds FK506 binding protein 4 ("FKBP4").

In a preferred embodiment, the compound that binds FKBP4 is selected from the group consisting of compounds of formula (I)

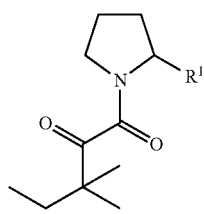

or a pharmaceutically acceptable salt or ester thereof, wherein R1 is COOH, a methoxy, a phenyl, a benzyl, a substituted phenyl or a substituted benzyl.

In a preferred embodiment the substituted phenyl and substituted benzyl of the compound of formula (I) are each individually substituted with an alkyl group, a methoxy group or a halogen.

In a more preferred embodiment the compound of formula (I) is selected from the group consisting of

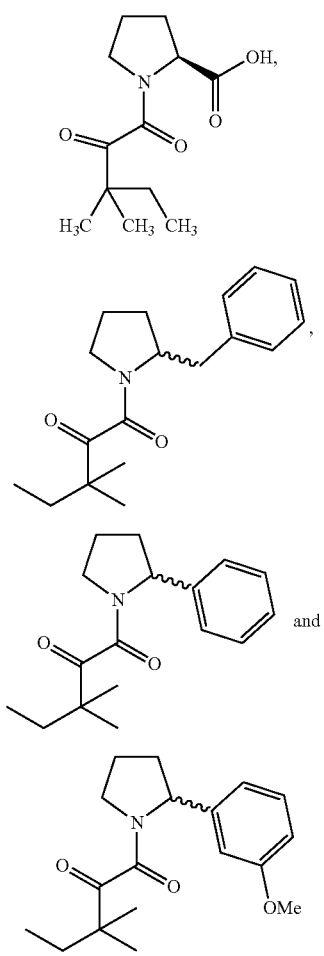

and a pharmaceutically acceptable salt or ester thereof.

In a most preferred embodiment the compound of formula (I) is RT175.

The present invention is further directed to a method of treating idiopathic pulmonary fibrosis comprising administering to a subject in need thereof an effective amount of a compositing containing a compound that binds FKBP4 and cyclosporine A.

In another embodiment, the present invention is directed to a method of treating idiopathic pulmonary fibrosis comprising administering to a subject in need thereof an effective amount of a composition comprising a compound that binds FKBP4 and concomitantly or sequentially administering a second composition comprising cyclosporine A.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
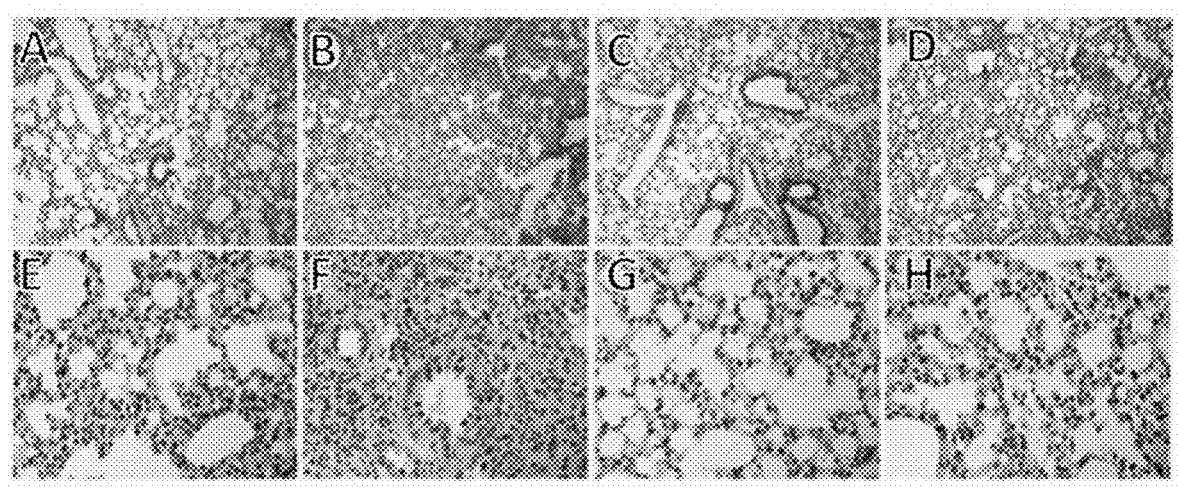
FIG. 1. Histology of mouse lung tissue 14 days after bleomycin-induced pulmonary fibrosis and following 10 days of treatment with RT175+cyclosporine A or vehicle. Panel A-D are at 10 times magnification and panels E-H are at 40 times magnification. Panels A and E are normal lung tissue, Panels B and F are affected lung tissue treated with vehicle. Panels C and G are affected lung tissue treated with RT175+cyclosporine inhalant. Panels D and H are affected lung tissue treated with a RT175+cyclosporine A intraperitoneal injection.

Applicants unexpectedly discovered that a composition containing a compound that binds FK506 binding protein 4 ("FKBP4") is surprisingly effective at treating idiopathic pulmonary fibrosis ("IPF"). Applicant further unexpectedly discovered that a composition containing a compound that binds FKBP4 and cyclosporine A is surprisingly effective at treating IPF.

As used herein, "RT175" refers to the compound of the formula,

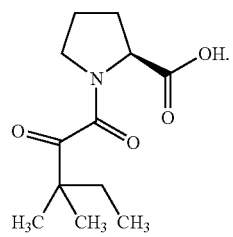

As used herein, "cyclosporine A" refers to the compound of the formula,

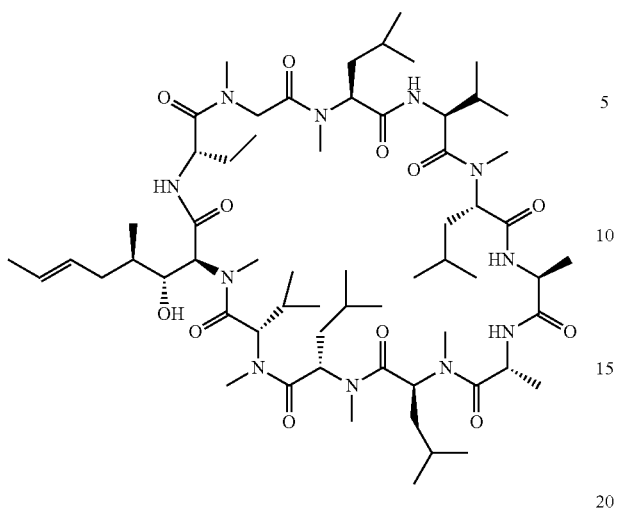

and any pharmaceutically acceptable salt or ester thereof.

As used herein the term "pharmaceutically acceptable" refers to ingredients that are not biologically or otherwise undesirable in a topical application.

As used herein the term "R1" refers to a substituent selected from the group consisting of COOH, a methoxy, a phenyl, a benzyl, a substituted phenyl and a substituted benzyl.

In general, the term "substituted" means that one or more hydrogens of the designated moiety are replaced with a suitable substituent.

As used herein the term "alkyl" refers to a branched or straight-chain alkyl consisting of a saturated hydrocarbon group of 1 to 24 carbon atoms (C1-C24) unless otherwise stated. The alkyl group can be cyclic or acyclic.

As used herein, the term "treat", "treating" or "treatment", refers to accomplishing one or more of the following: (a) reducing the severity of a disorder; (b) limiting the development of symptoms characteristic of a disorder being treated; (c) limiting the worsening of symptoms characteristic of a disorder being treated and (d) abrogating symptoms characteristic of a disorder being treated. The term "treat", "treating" or "to treat" includes abrogating, substantially inhibiting, slowing or reversing the progression of a disease, condition or disorder, substantially ameliorating clinical or esthetical symptoms of a condition, substantially preventing the appearance of clinical symptoms of a disease, condition, or disorder.

The present invention is directed to a method of treating idiopathic pulmonary fibrosis comprising administering to a subject in need thereof an effective amount of a composition containing a compound that binds FK506 binding protein 4 ("FKBP4").

In a preferred embodiment, the compound that binds FKBP4 is selected from the group consisting of compounds of formula (I)

(I)

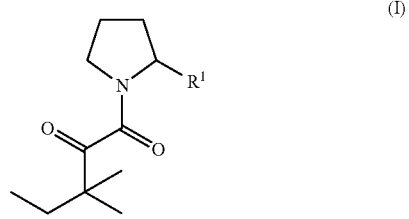

or a pharmaceutically acceptable salt or ester thereof, wherein R1 is COOH, a methoxy, a phenyl, a benzyl, a substituted phenyl or a substituted benzyl.

In a preferred embodiment the substituted phenyl and substituted benzyl of the compound of formula (I) are each individually substituted with an alkyl group, a methoxy group or a halogen.

In a more preferred embodiment the compound of formula (I) is selected from the group consisting of ("RT175")

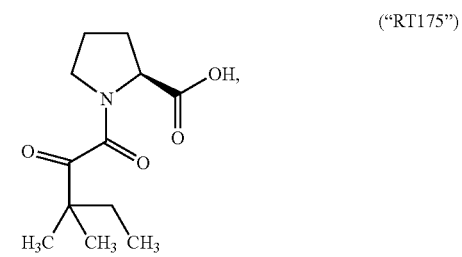

("RT1061")

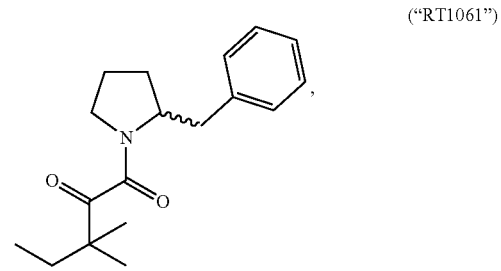

("RT1062")

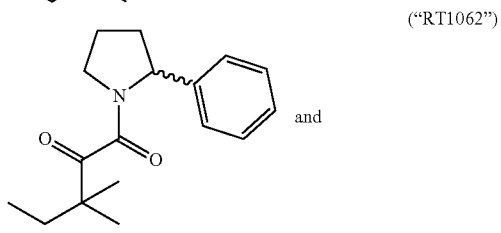

and ("RT1063")

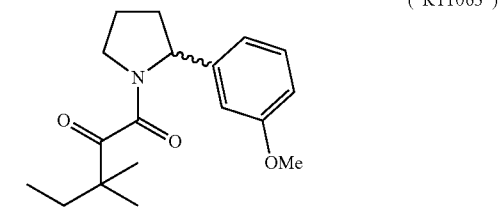

and a pharmaceutically acceptable salt or ester thereof.

In a most preferred embodiment the compound of formula (I) is RT175.

The present invention is further directed to a method of treating idiopathic pulmonary fibrosis comprising administering to a subject in need thereof an effective amount of a compositing containing a compound that binds FKBP4 and cyclosporine A.

In another embodiment, the present invention is directed to a method of treating idiopathic pulmonary fibrosis comprising administering to a subject in need thereof an effective amount of a composition comprising a compound that binds FKBP4 and concomitantly or sequentially administering a second composition comprising cyclosporine A.

In a preferred embodiment, compositions of the present invention further comprise a pharmaceutically acceptable carrier.

The following examples are for are provided solely for illustrative purposes and are not meant to limit the invention in any way.

EXAMPLES

Example 1. Synthesis of RT1061

The following methods are used for the synthesis of either the (S)-isomer, (R)-isomer or racemic (i.e., (R,S)-isomers) compounds shown in Scheme I depending on the chirality of the starting materials. If (S)-prolinol was used to synthesize compound 4 then all resulting compounds were the (S)-isomer. If (R)-prolinol was used to synthesize compound 4 then all resulting compounds were the (R)-isomer. If both (S) and (R)-prolinol were used to synthesize compound 4 then all resulting compounds were racemic.

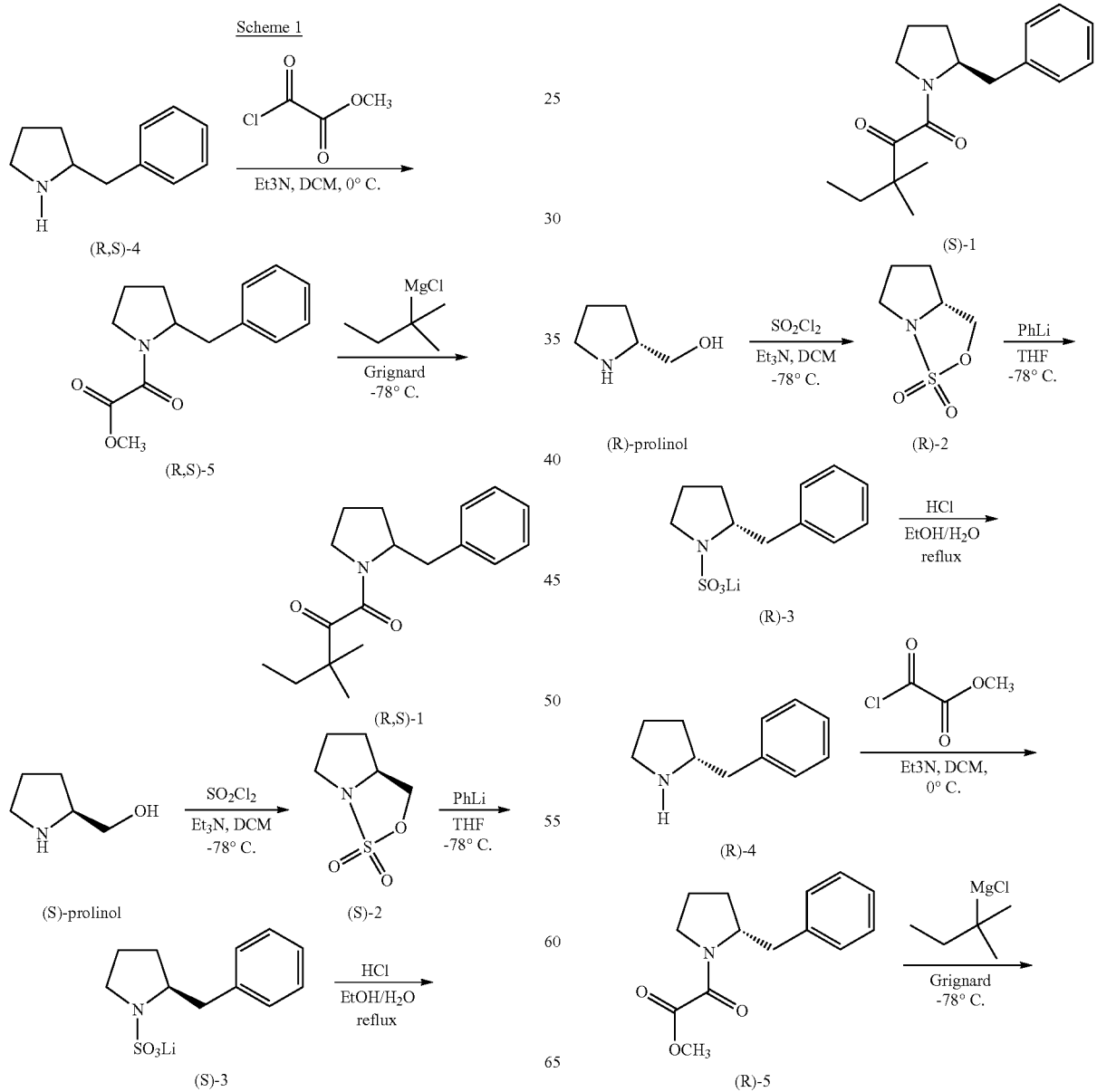

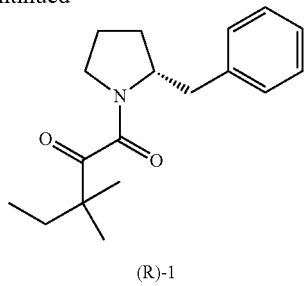

(R)-1

Synthesis of (S)-2-Benzyl pyrrolidine (Compound (S)-4) from (S)-prohnol

A preparation of sulfamidate (method of Alker, D.; Doyle, K. J.; Harwood, L. M.; McGregor, A.; Tetrahedron Asymmetry 1990, 1, 877.) (S)-prolinol (Aldrich) (2.62 g, 25.2 mmol) and triethylamine ("Et3N"; 7.0 mL, 50.0 mmol) were dissolved in 150 mL dry dichloromethane ("DCM") under argon in a 500 mL round bottom flask and cooled to −78° C. To this mixture was added sulfuryl chloride ("$SO_2Cl_2$"; 2.1 mL, 25.9 mmol) in 150 mL dry dichloromethane dropwise over 45 minutes and stirred at −78° C. for 3 hours then allowed to warm to room temperature and stirred overnight. The mixture was washed 0.1 N HCl (3×75 mL), brine (75 mL), dried over sodium sulfate, filtered and the solvent removed via vacuum resulting in the sulfamidate (Compound (S)-2) a yellow oil (2.66 g).

The crude product was purified by applying to a dry silica cartridge (Analogix, 40 g) in 7 mL dichloromethane and eluting with a stepwise gradient of ethyl acetate in hexanes (0, 10, 20%). The fractions containing product were combined and concentrated to dryness. Upon further drying colorless crystals formed to yield 1.36 g (33%) of compound (S)-2. The product was characterized by 1H NMR and ms (APCI) 164 (M+H)+.

Bromobenzene (0.265 mL, 2.53 mmol) was dissolved in 2 mL dry THF in a 10 mL round bottom flask under argon and cooled to −78° C. n-Butyllithium (0.96 mL of 2.5 M solution in hexanes, 2.40 mmol) was added via syringe over 40 minutes and the reaction was stirred for 1 h at −78° C. 0.326 g (2.00 mmol) of 2 in 1.5 mL THF was added to this mixture via syringe over 10 minutes and the reaction was allowed to warm to room temperature and stirred overnight. The reaction was quenched with a few drops of water and the solvent removed via vacuum to yield a tan viscous oil (compound 3). This residue was dissolved in 10 mL of a 1:1 solution of 2 N HO/ethanol and heated at reflux for 22 hours. After cooling the ethanol was removed via vacuum, 5 mL 0.1 N HCl added and the aqueous solution was extracted with ethyl acetate (3×5 mL). The pH of the aqueous solution was adjusted to >10 with 50% sodium hydroxide ("NaOH") and extracted with ethyl acetate (4×5 mL). The ethyl acetate layers were combined and washed with brine, dried and the solvent removed via vacuum resulting in 0.262 g of compound (S)-4 a light brown oil (81%). The product was characterized by 1H NMR and ms (ESI): 162 (M+H)+.

Synthesis of (R)-2-Benzyl pyrrolidine (Compound (R)-4) from (R)-prohnol

The same procedures were followed as in the synthesis of (S)-2-Benzyl pyrrolidine (compound (S)-4) from (S)-prolinol except (R)-prolinol was substituted for (S)-prolinol.

Synthesis of Methyl 2-(2-benzylpyrroldine-1-yl)-2-oxoacetate (Compound 5)

52 milligrams ("mg"; 0.324 millimoles ("mmol")) of 2-benzylpyrrolidine (compound 4; ASDI Inc.) was dissolved in 2 milliliters ("mL") dry dichloromethane in a 2 dram vial and cooled to 0° C. Triethylamine (68 μL, 0.488 mmol) and methyl chlorooxoacetate (47 μL, 0.485 mmol) were added and the reaction stirred at 0° C. for 1 hour and then room temperature overnight. The reaction mixture was diluted with 5 mL dichloromethane, washed with 0.1 N HCl (3×3 mL), saturated sodium bicarbonate solution (3×3 mL), dried and the solvent removed via vacuum to yield 61 mg of compound 5 as a tan viscous oil (76%). The product was characterized by 1H nuclear magnetic resonance ("NMR") spectroscopy and liquid chromatography-mass spectrometry ("lc/ms"; ESI): 248 (M+ and used directly for the next reaction.

Synthesis of 1-(2-benzylpyrrolidin-1-yl)-3,3-dimethylpentane-1,2-dione (Compound 1; RT1061)

61 mg (0.247 mmol) of compound 5 was dissolved in 2 mL dry tetrahydrofuran ("THF") under argon in a 2-dram vial fitted with a Teflon® septa cap and cooled to −78° C. 0.37 mL of 1,1-dimethylpropane magnesium chloride (1 M ether solution, Aldrich) was added via syringe and the reaction stirred at −78° C. for 2 hours and then allowed to warm to room temperature and stirred overnight. The reaction was quenched by the addition of aqueous ammonium chloride and the aqueous mixture was extracted with ethyl acetate (3×5 mL). The ethyl acetate was washed with brine (1×), dried and the solvent removed via vacuum to yield a light tan oil. The product (compound 1) was purified by applying an ethyl acetate solution to a dry silica cartridge (Analogix, 4g) and eluting with hexanes and then 2% ethyl acetate/hexanes. 35 mg of compound 1 as a colorless viscous oil was isolated and characterized by 1H NMR and lc/ms (ESI): 288.1 (M+H)+.

Enantiomeric Purity

The enantiomeric purity of the compounds at the key stage of the 2-benzylpyrrolidine isomers (compound 4) was estimated using Mosher's reagent to produce the diastereomeric Mosher amides, which were separable by high pass liquid chromatography and indicated that the synthesis of the chiral compounds 4 proceeded to give compounds of >95% isomeric purity. (method of J. A. Dale, D. L. Dull, H. S. Mosher (1969). "α-Methoxy-α-trifluoromethylphenylacetic trifluoromethylphenylacetic acid, a versatile reagent for the determination of enantiomeric composition of alcohols and amines". Journal of Organic Chemistry 34 (9): 2543-2549.

Example 2. Treatment of Bleomycin-Induced Pulmonary Fibrosis in Mice

Method

The studies were carried out in adult C57/B16 mice. The animals were allowed to acclimatize for at least 48 hours before the study was initiated. Pulmonary fibrosis was initiated by intraperitoneal ("ip") injection of the antineoplastic agent bleomycin at 3 mg/kg in phosphate buffered saline ("PBS") (day 0). PBS alone was used as a control. RT175+cyclosporine A ("RT1840") was dissolved in sterile PBS, and the solution was sterile filtered. On the fourth day following bleomycin injection, treatment was initiated with either inhaled RT1840 (20 μl of 1mg/ml RT1840), ip injection of 5 mg/kg RT1840, or inhaled vehicle. The animals were treated daily for 10 days, and then sacrificed on the day following the final treatment (day 14). (n=3 animals/group, except inhaled RT1840, in which n=4).

The animals were evaluated for their physical appearance on the day of sacrifice. The gross appearance of the lungs was examined within moments of sacrifice and rated on a scale of 0 to 4+. The lungs were perfused to clear them of blood. One lung was split with one portion snap frozen in optimum cutting temperature formulation for frozen section histology and trichrome staining and the other portion was immersion fixed in 4% paraformaldehyde in PBS for immunocytochemistry, and the other lung was taken for biochemical analysis.

The tissue was deparaffinized, rehydrated and stained with a mAb against smooth muscle actin ("SMA") (Sigma) followed by amplification with Vectastain ABC elite strepavidin, and then biotinylated species-specific second antibody (Vector). Finally, the tissue was dehydrated, mounted in Permount (Sigma) and coverslipped. The extent of SMA fibroblast invasion of the lung was evaluated by counting the number of SMA+ cells/field over 25 to 60 fields per section, 2 sections/slide, 1 slide per animal, and averaging the number of SMA+ cells for each treatment animal. The data were binned into groups from 0 to 4+: 1+ (11-20 SMA+ cells/field), 2+ (21-30 SMA+ cells/field), 3+ (31-40 SMA+ cells/field), and 4+(>41 SMA+ cells/field).

Results

Clinical Evaluation

On the 14th day after bleomycin injury the mice were observed for the extent of clinical disease and gross pathology of the tissue. The vehicle-treated mice appeared ill. They were tachypnic, their fur was poorly groomed, they neither explored their surroundings, nor did they exhibit escape behavior. In contrast, there was no way to discern between the RT1840-treated animals, irrespective of the route of administration, and the animals without bleomycin treatment. These animals were well groomed, showed no signs of labored breathing and moved about the cage exploring their environment.

The animals were sacrificed, and the appearance of their lungs was assessed for hypertrophy and gross signs of fibrosis, including a mottled appearance, all on scales of 0 to 4+. The clinical assessment of the animals was a good predictor of the presence or absence of gross pathology in the lungs. The RT1840-treated animals showed 0 to 1+ pulmonary hypertrophy, and 0 to 1+ mottling. In contrast, the lungs of the vehicle-treated animals were mottled, grossly hypertrophic, with 3+ fibrosis and the tissue was friable. The clinical and gross pathologic evaluations are summarized in Table 1.

TABLE 1

| Treatment | Physical Evaluation | Gross Lung Appearance |
| --- | --- | --- |
| RT1840 Inhaled | Appeared well; noted attempts to escape | 0-1+ hypertrophy; 0-1+ gross fibrosis |
| RT1840 Intraperitoneal Injection | Appeared well; noted attempts to escape | 0-1+ hypertrophy; 0-1+ gross fibrosis |
| Vehicle Inhaled | Tachypnic; appeared ill and listless | Mottled; gross fibrosis; 3+ hypertrophy; friable |
| Control | Appeared well; noted attempts to escape | White, elastic, normal appearance |

Histology of Lung Tissue

Fourteen days after insult, the lungs were harvested, and a portion was flash frozen cryosectioned and stained with either hematoxylin and eosin stain or trichrome. The difference in histology between the lung tissues from bleomycin treated animals treated with inhaled vehicle or inhaled RT1840 was dramatic. There were very few visible alveoli in the inhaled vehicle treated lung while the inhaled RT1840 treated lung had a mostly-normal appearance. See, FIG. 1, comparing panels B and F with panels C and G. Parenteral treatment with RT1840 also has a strong therapeutic effect on the fibrotic lung. See, FIG. 1, panels D and H. The near normal appearance of the inhaled RT1840 and intraperitoneal RT1840 treated lungs compared with lung tissue that was never exposed to bleomycin demonstrates the positive extent of RT1840 treatment on the structure of the diseased lung. See, FIG. 1, comparing panels A and E with panels C, D, G and H.

Figure 2:
FIG. 2. Trichrome staining of lung tissue 14 days after bleomycin-induced pulmonary fibrosis and following 10 days of treatment with RT175+cyclosporine A or vehicle. Panel A is normal lung tissue. Panel B is affected lung tissue treated with vehicle. Panel C is affected lung tissue treated with RT175+cyclosporine inhalant. Panel D is affected lung tissue treated with a RT175+cyclosporine A intraperitoneal injection.

Trichrome staining of the lung tissue described above accurately reflected the histologic analysis shown in FIG. 1. The interstitial collagen disposition was virtually identical in tissue that was never exposed to bleomycin and the lung tissue from animals treated with RT1840, irrespective of route of administration. See, FIG. 2, comparing panel A to panels C and D. Collagen staining with trichrome revealed a lace-like scar spread through the pulmonary parenchyma, a characteristic of pulmonary fibrosis, only in the inhaled vehicle treated tissue. See, FIG. 2, panel B.

Fibroblasts in the Fibrotic Lung

Figure 3:
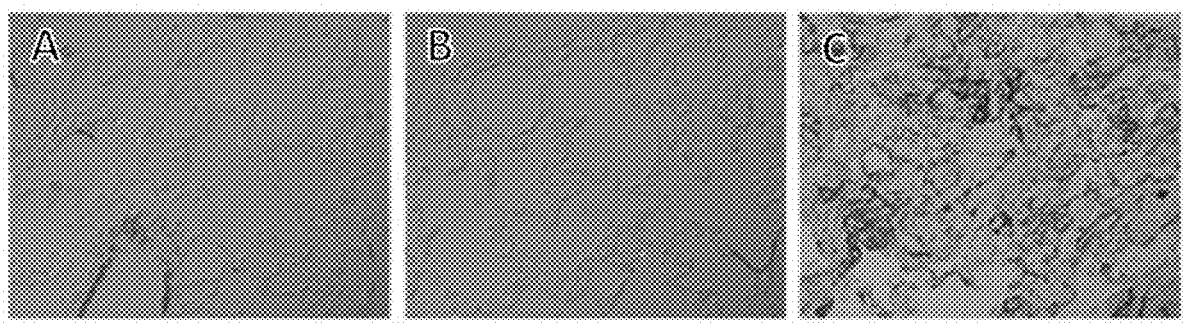
FIG. 3. Qualitative analysis of smooth muscle actin-positive fibroblast in the lungs of RT175+cyclosporine A and vehicle treated mice. Panel A is affected lung tissue treated with RT175+cyclosporine inhalant. Panel B is affected lung tissue treated with a RT175+cyclosporine A intraperitoneal injection. Panel C is affected lung tissue treated with vehicle.

As demonstrated above, there is a significant remodeling of the pulmonary architecture in the setting of fibrosis. A hallmark of these changes is the concomitant destruction of alveolar structures and a migration/proliferation of pulmonary fibroblasts. Therefore, quantitation of the number of fibroblasts is a validated surrogate of the extent of fibrotic disease. We stained the lung tissue described above with a monoclonal antibody that recognizes smooth muscle actin ("SMA"), which is expressed by fibroblasts/myofibroblasts, and quantified the number of SMA-positive cells found in the lung. There was a direct correlation between the number of fibroblasts and the extent of damage shown by hematoxylin and eosin or trichrome staining shown in FIGS. 1 and 2, respectively. See, FIG. 3, comparing panel C with panels A and E of FIG. 1 and panel A of panel B and comparing panel A with panels C and G of FIG. 1 and panel C of FIG. 2 and comparing panel C with panels D and H of FIG. 1 and panel D of FIG. 2.

CONCLUSION

The data above have shown that after a 4-day establishment of bleomycin-induce pulmonary fibrosis in adult mice, administration of inhaled or intraperitoneally administered RT1840 over the following days arrests and appears to reverse the disease progression. The clinical evaluation of the animals and the gross appearance of the lungs are consistent with attenuated disease in the RT1840 treated animals. In addition, the histology of RT1840-treated lung tissue is virtually identical with the control lung tissue that had not had bleomycin-induced disease. See, FIG. 1, comparing panels A and E with C, D, G and H. At the biochemical level, treatment with RT1840 either prevented or reversed the accumulation of collagen in the pulmonary interstitium, while the collagen deposited in the inhaled vehicle treated lung tissue has a fine, lacy appearance throughout. See, FIG. 2, comparing panels C and D with panel B. Finally, consistent with the collagen accumulation in the inhaled vehicle treated lung tissue, there is an extensive accumulation of SMA-positive fibroblasts, while these cells are minimally present in the RT1840-treated lungs. See, FIG. 3, comparing panel C with panels A and B. Taken together, these data demonstrate that RT1840 treatment of the damaged lung leads to the re-establishment of normal ECM, the rapid clearance and/or prevention of cellular infiltration and the establishment and/or maintenance of normal cellular relationships.

What is claimed is:

1. A method of treating idiopathic pulmonary fibrosis comprising administering to a patient in need thereof an effective amount of a composition comprising a compound of formula (I)

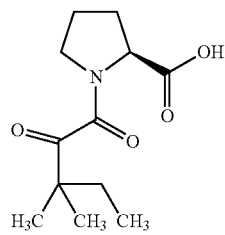

(I)

and cyclosporine A.

2. The method of claim 1, wherein the composition is administered via inhalation.

3. The method of claim 1, wherein the composition is administered via intraperitoneal injection.

4. A method of treating idiopathic pulmonary fibrosis comprising administering to a subject in need thereof a composition comprising a compound of formula (I)

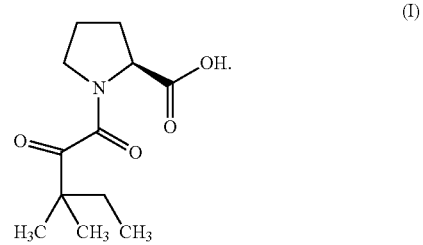 [SMILES: CCC(C)(C)C(=O)C(=O)N1CCC[C@H]1C(=O)O]

(I)

and concomitantly or sequentially administering a second composition comprising cyclosporine A.

* * * * *